(12) United States Patent
Ahn et al.

(10) Patent No.: US 7,601,269 B2
(45) Date of Patent: Oct. 13, 2009

(54) ON-CHIP SAMPLE PREPARATION FOR WHOLE BLOOD ANALYSIS

(76) Inventors: Chong H. Ahn, 8507 Capricorn Dr., Cincinnati, OH (US) 45249; Aniruddha Puntambekar, 4326 Windrift Ct., Mason, OH (US) 45040; Alok Jain, 2454 Leslie Cir., Ann Arbor, MI (US) 48105; Jungyoup Han, 10854 Lakehurst Ct., Cincinnati, OH (US) 45242

( * ) Notice: Subject to any disclaimer, the term of this patent is extended or adjusted under 35 U.S.C. 154(b) by 0 days.

(21) Appl. No.: 12/327,204

(22) Filed: Dec. 3, 2008

(65) Prior Publication Data
US 2009/0152215 A1  Jun. 18, 2009

Related U.S. Application Data

(62) Division of application No. 10/946,685, filed on Sep. 22, 2004, now Pat. No. 7,476,326.

(60) Provisional application No. 60/506,641, filed on Sep. 26, 2003, provisional application No. 60/506,226, filed on Sep. 26, 2003, provisional application No. 60/506,321, filed on Sep. 26, 2003, provisional application No. 60/506,424, filed on Sep. 26, 2003, provisional application No. 60/506,635, filed on Sep. 26, 2003.

(51) Int. Cl.
*B01D 37/00* (2006.01)
*B01L 11/00* (2006.01)

(52) U.S. Cl. .................. 210/767; 210/348; 422/100; 422/101; 422/103; 422/104

(58) Field of Classification Search ............ 210/348, 210/767; 422/100, 101, 102, 103, 104, 177
See application file for complete search history.

(56) References Cited

U.S. PATENT DOCUMENTS

RE31,688 E  *  9/1984  Popovich et al. ........... 604/6.01

(Continued)

FOREIGN PATENT DOCUMENTS

EP      0520185     *  5/1992

(Continued)

OTHER PUBLICATIONS

Lin, et al, Journal of Membrane Science, vol. 173, p. 73-85 (2000).*

(Continued)

*Primary Examiner*—John Kim
(74) *Attorney, Agent, or Firm*—Joseph F. Aceto; James L. Wilcox

(57) ABSTRACT

A novel filter-less separation technique for separating suspended particles from a solution is disclosed. More specifically, an on-chip bioparticle separator is disclosed, which relies on the differential force exerted by application of a series of high magnitude, short duration pressure pulses on bioparticles in suspension within microchannels, resulting in separation of suspended bioparticles. The filter-less separation technique is inherently suited to μTAS (Micro Total Analysis System) since it exploits uniquely microscale phenomena to achieve separation. The on-chip bioparticle separator can be easily integrated with a disposable biochip, can be fabricated using low-cost, rapid manufacturing techniques, and can provide high performance for separation of bioparticles without the use of specialized or expensive equipment. Embodiments of the present invention address a significant challenge in the development of disposable microfluidic biochips, specifically, providing a reliable solution for separating bioparticles in a microfluidic system that may be immediately applied for a variety of microfluidic biochip applications.

11 Claims, 12 Drawing Sheets

U.S. PATENT DOCUMENTS

| | | | |
|---|---|---|---|
| 4,619,639 A * | 10/1986 | Nose et al. | 604/8 |
| 5,906,570 A * | 5/1999 | Langley et al. | 494/45 |
| 5,914,042 A * | 6/1999 | Ball et al. | 210/650 |
| 6,315,707 B1 * | 11/2001 | Smith et al. | 494/37 |
| 7,179,423 B2 * | 2/2007 | Bohm et al. | 422/100 |
| 7,211,442 B2 * | 5/2007 | Gilbert et al. | 436/177 |
| 2004/0011651 A1 * | 1/2004 | Becker et al. | 204/547 |
| 2004/0018611 A1 * | 1/2004 | Ward et al. | 435/287.2 |

FOREIGN PATENT DOCUMENTS

| | | | |
|---|---|---|---|
| WO | WO97/20207 | * | 6/1997 |
| WO | WO98/39379 | * | 9/1998 |

OTHER PUBLICATIONS

Malchesky, P.S., Therapeutic Apheresis, vol. 5(4), p. 270-282 (Aug. 2001).*

Svoboda, J., Journal of Magnetism and Magnetic Materials, vol. 220, No. 2-3, pp. 103-105 (Oct. 2000).*

Puntambekar, et al., Proceedings of the 7th International Conference on Micro Total Analysis Systems (micro-TAS 2003), pp. 1017-1020, (Oct. 5-9, 2003).*

Cousins, et al., Ultrasonics, vol. 38 (2000), pp. 654-656.*

* cited by examiner

ON-CHIP SAMPLE PREPARATION FOR WHOLE BLOOD ANALYSIS

CROSS-REFERENCE TO RELATED APPLICATIONS/INCORPORATION BY REFERENCE

This application is a divisional application of U.S. patent application Ser. No. 10/946,685 filed Sep. 22, 2004 now U.S. Pat. No. 7,476,326 and claims priority to provisional U.S. Patent Applications Ser. Nos. 60/506,641; 60/506,226; 60/506,321; 60/506,424; and 60/506,635 all filed on Sep. 26, 2003, and all of which are incorporated herein by reference in their entirety.

This patent application incorporates U.S. Ser. No. 10/946,818 herein by reference in its entirety.

TECHNICAL FIELD

Embodiments of the present invention generally relate to the development of filter-less separation techniques for separating blood cells and plasma from a whole blood sample. This technique can be applied to separation of microparticles (or microspheres) from a particle-laden liquid by applying a series of pressure pulses to a suspended solution. This approach is particularly relevant for lab-on-a-chip applications wherein conventional separation processes such as centrifugation or filtering are difficult to implement.

BACKGROUND OF THE INVENTION

Microfluidic systems for biochemical analysis are generally composed broadly of the following components: fluid channels to guide fluid flow, microvalves to regulate fluid flow, a pressure source to cause fluidic displacement, and biosensors to detect relevant parameter. Biosensors are biological sensors which, depending on their application, measure a particular parameter in a bodily fluid such as blood.

An analyte frequently in use for various diagnoses, blood, is a non-Newtonian fluid transporting oxygen, carbon dioxide, nutrients, salts, hormones, metabolites and various other components. The most important components of blood, from a rheological point of view, are plasma and RBC's (red blood cells). RBC's take up about half the volume of whole blood and significantly impact the flow characteristics of blood. Blood plasma thus accounts for about half the volume of whole blood. The plasma itself is about 95% (w/w) water. The rest is proteins, minerals, vitamins, glucose etc.

Quite often, biosensors need to deal with irrelevant or unwanted components in the sensed solution. For example, in a microfluidic device to measure blood glucose level, the sensor where the electrochemical reaction takes place frequently experiences interference from microparticles like red blood cells, thereby reducing its efficiency and possibly increasing reaction time. In other cases, the microparticles might cause interference during detection by optical means due to obstruction of projected light. The separation of these microparticles from the remainder of the suspension solution is thus often desirable.

The most common methods in use to achieve separation of bioparticles, in lab-on-a-chip or μTAS systems, have been physical filtration and less commonly, centrifugation. U.S. patents USRE31688, U.S. Pat. No. 5,914,042, U.S. Pat. No. 5,906,570, and U.S. Pat. No. 4,619,639, incorporated in their entirety by reference herein, describe some of the different types of membrane filtration methods. The underlying principle in this technique is to cause separation of blood into its constituents by making it flow through a membrane filter with a number of pores having micrometer-range dimensions. According to the purpose of the device, the pore size of the membranes is varied, ranging from approximately, 0.5 micron diameter to 5 micron diameter. In the case of a very small pore size, some positive pressure might be required to make the solution cross the membrane. There are a number of membrane materials and compositions in use. Patent applications WO9839379A1, WO9720207A1, and WO7901121A1 describe some more membrane methods.

The other major technique for separation is by using centrifugal force applied to the suspension solution causing separation depending on the specific mass and gravities of the particles which compose the solution. The solution is contained in a chamber and rapidly rotated at high angular speed, which causes application of the centrifugal force. U.S. Pat. No. 6,315,707 and European patent application EP0520185A1 describe centrifugation methods. Another method, Field Flow Fractionation is mentioned in U.S. patent application UA20040011651A1. Here, the solution containing the microparticles is made to flow through a separation channel or chamber where an applied electric or thermal field causes fractionation or separation of the particles due to the field gradient across the width of the channel. Depending on their charge or temperature response, particles are drawn to the top or bottom of the channel and the remaining solution can be suitably extracted. U.S. patent application US20040018611A1 deals with yet another method for particle separation utilizing the effects of a High Gradient Magnetic Separation (HGMS). Particles are either tagged with magnetic particles, or simply subjected to a magnetic field and thus separated based on their magnetic response. Another technique to efficiently separate blood cells from plasma is to cause aggregation of blood cells by exposure of whole blood to an ultrasonic standing wave as described in Cousins et al, "Clarification of plasma from whole human blood using ultrasound," Ultrasonics, Vol. 38, 2000. When this is done, the cells concentrate into clumps at radial separations of half wavelengths. The clumps grow in size and sediment under gravity and a distinct plasma/cell interface forms as cells sediment.

However, centrifugation is too bulky for point-of-care handheld detection equipment. It is laboratory specific and time-consuming. Magnetic separation and Field flow fractionation require the use of specialized equipment as does Ultrasonic separation. These techniques are generally more expensive than the other methods. Membrane filtration is suitable for disposable, point-of-care applications but the inherent problems have been aggregation and fragility of materials. The fabrication of the membranes and the subsequent integration of membranes into existing devices can be a complicated process. It is also relatively more time-consuming. Furthermore, membrane filtration techniques are also more expensive and require high pressures and/or specialized fluid driving.

No known technique has been able to achieve the characteristics of bioparticle separation with an easy and low-cost method.

SUMMARY OF THE INVENTION

Certain embodiments of the present invention seek to address the shortcoming listed above. Disclosed herein are the techniques used for on-chip bioparticle separation using a series of pressure pulses and its application for disposable biochips.

Disclosed herein is a novel filter-less separation technique for separating suspended particles from solution. Embodiments of the present invention overcome many of the disadvantages of the prior art by providing an on-chip bioparticle separator using a series of pressure pulses that is small in size, easy to fabricate, more reliable (since it has no moving parts or complex control equipment), low cost, and has a simpler actuation/control circuit than conventional separation techniques.

Specifically, disclosed herein is a novel on-chip bioparticle separator using a series of pressure pulses, one such pressure pulses having high amplitude and short duration, and which can be fabricated as a fully integrated component of a microfluidic biochemical analysis system, which is suitable for disposable, point-of-care applications.

Further disclosed herein are techniques to apply a series of pressure pulses to the microfluidic biochip. The bioparticle separator using a series of pressure pulses is ideally suited towards microfluidic applications and cart be easily controlled by changing a number of parameters such as a number of pulses, pressure magnitude, rise and fall times of the pressure pulses, and the duration of the pressure pulses (including multi-stage profile of pulses). Control of the pressure profile characteristics can be achieved by any pressure source regulated from a computer using programs such as LabVIEW™ or by using a dedicated electronic controller.

In accordance with an embodiment of the present invention, the choice of the pressure sources is a pressurized tank filled with biochemically inert gas, specifically nitrogen which does not react with any of the biochemical microfluidic samples. However, as will be readily apparent, other gases may also be used for this application including in certain cases, gases (such as oxygen) which will actually promote (or impede) a given biochemical reaction.

The bioparticle separator using a series of pressure pulses can be easily fabricated and integrated on a wide variety of substrate materials typically used for biochip applications such as Silicon, Silicon derived surfaces such as Silicon Dioxide, Silicon Carbide or Silicon Nitride, Glass, injection molded or embossed polymer substrates, polymer laminates or thin films, and ceramics.

Without intent of limiting the scope of application of the present invention, the application of the present invention is generally a low-cost, disposable plastic biochip for biochemical analysis, wherein the bioparticle separator is a fully integrated component of the biochip.

Certain embodiments of the present invention overcome the deficiencies and inadequacies in the prior art as described in the previous section and as generally known in the industry.

Certain embodiments of the present invention provide a technique for bioparticle separation, from a suspension solution, wherein the aforementioned technique is fully compatible with the techniques and methodology commonly used with biochips and can serve as a fully-integrated portion of the biochip.

Also disclosed herein is a means of generating the requisite pressure pulses for achieving separation of bioparticles from a suspension wherein the pressure generation system is not a part of the biochip, in accordance with an embodiment of the present invention.

Further disclosed herein is a means of generating the requisite pressure pulses for achieving separation of bioparticles from a suspension, wherein the pressure generation system is a fully-integrated component of the biochip, in accordance with an embodiment of the present invention.

Certain embodiments of the present invention achieve filter-less separation of bioparticles from suspension by using a plurality of pressure pulses, wherein the amplitude, duration, nature and periodicity of the pressure pulses is altered to achieve separation.

Certain embodiments of the present invention provide a multitude of pressure pulse profiles, which may be used for achieving separation of bioparticles from a suspension.

Other features and advantages of the present invention will become apparent from the detailed description of various embodiments of the present invention when considered in conjunction with the accompanying drawings.

BRIEF DESCRIPTION OF THE DRAWINGS

The present invention, as defined in the claims, can be better understood with reference to the following drawings and microphotographs of the actual devices. The drawings are not all necessarily drawn to scale, emphasis instead being placed upon clearly illustrating principles of the present invention.

DETAILED DESCRIPTION OF THE INVENTION

Figure 1A:
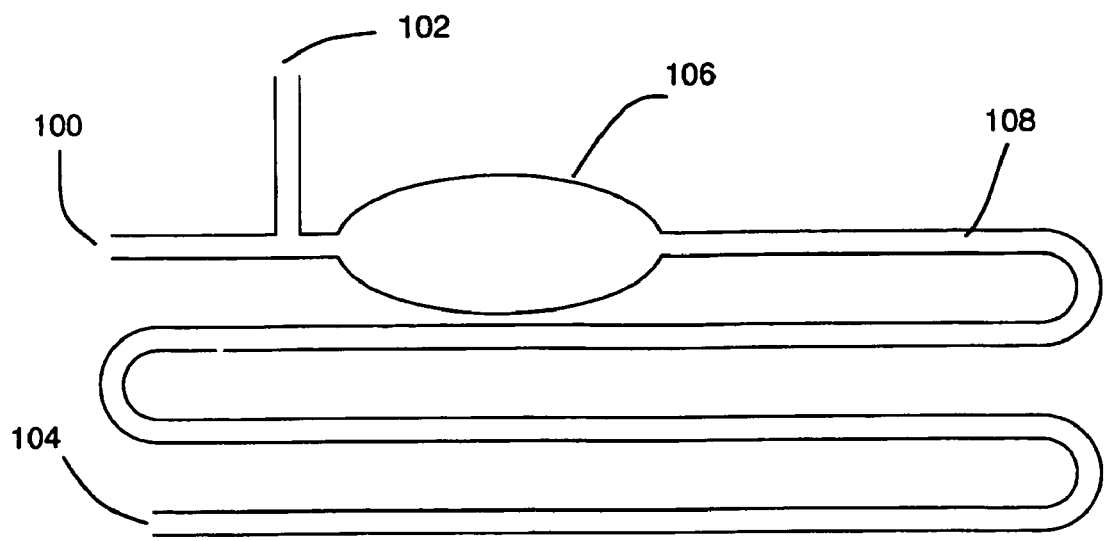
FIGS. 1$a$-1$g$ are a schematic illustration of the operation of the on-chip bioparticle separator using a series of pressure pulses in conjunction with a microfluidic system and also a schematic view of the pressure profile used therewith, in accordance with an embodiment of the present invention.
Figure 1B:
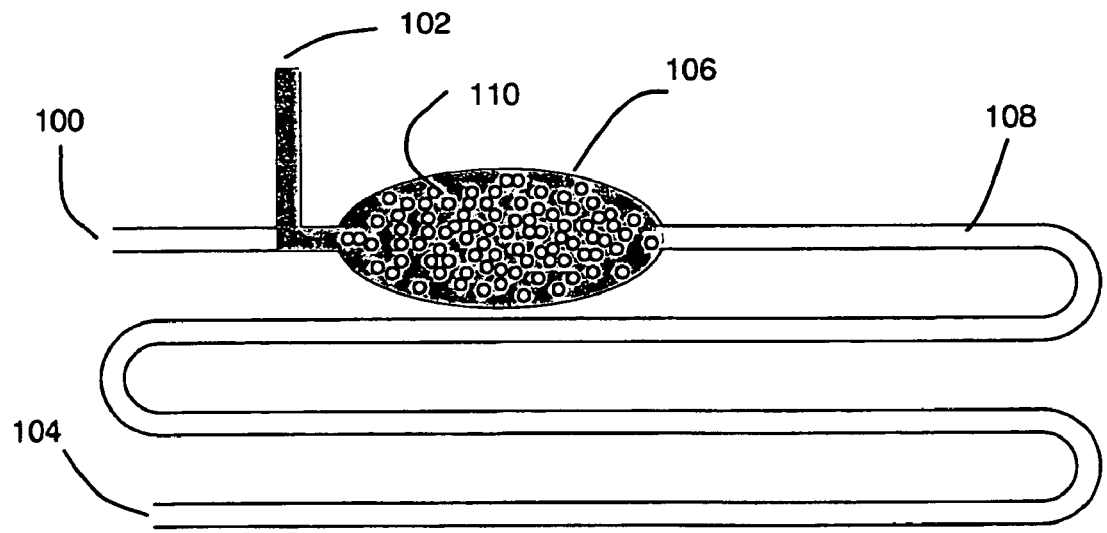
Figure 1C:
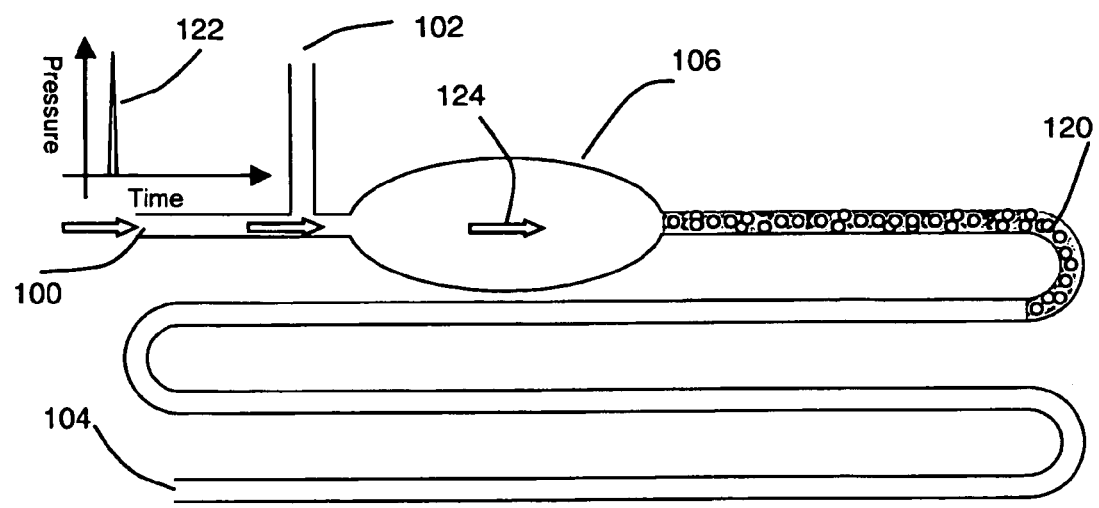
Figure 1D:
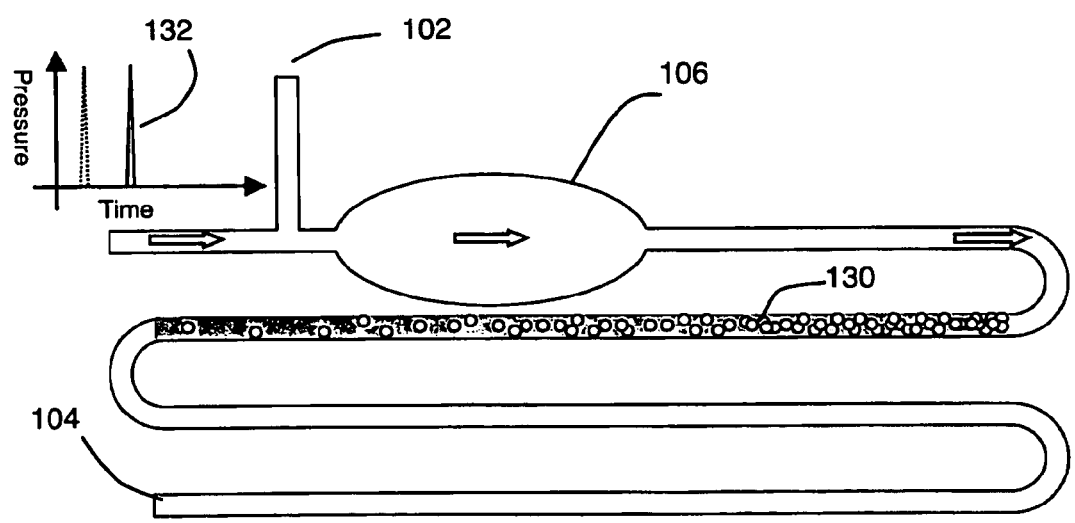
Figure 1E:
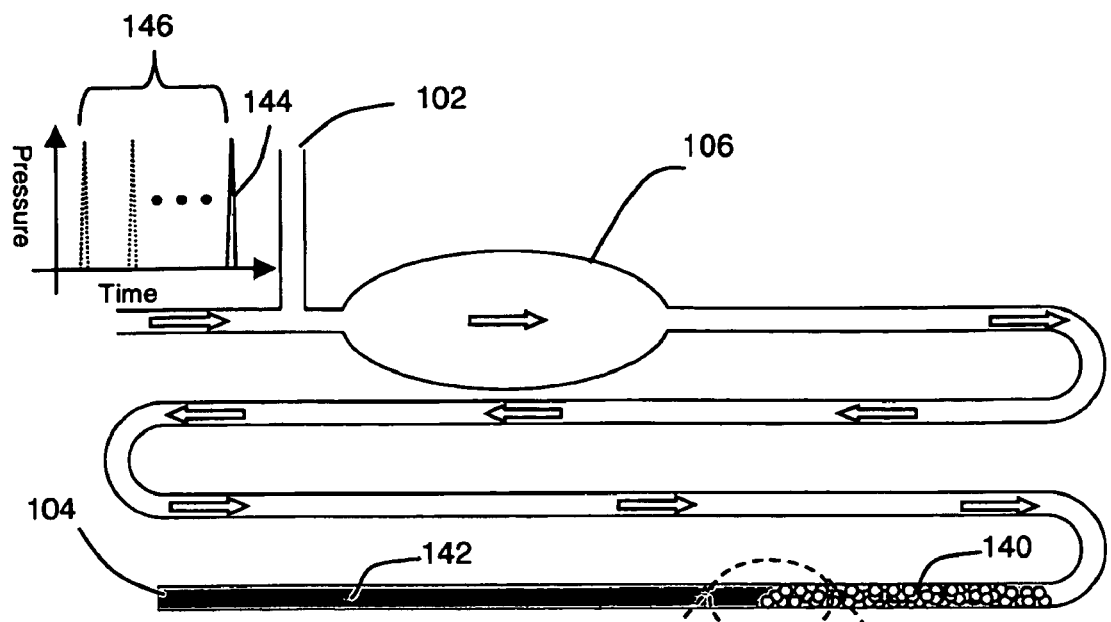
Figure 1F:
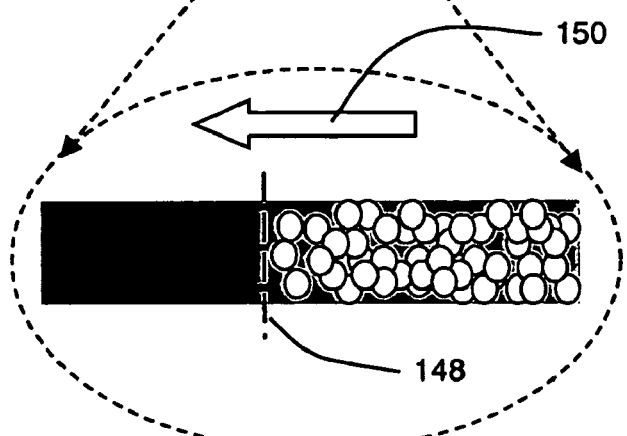
Figure 1G:
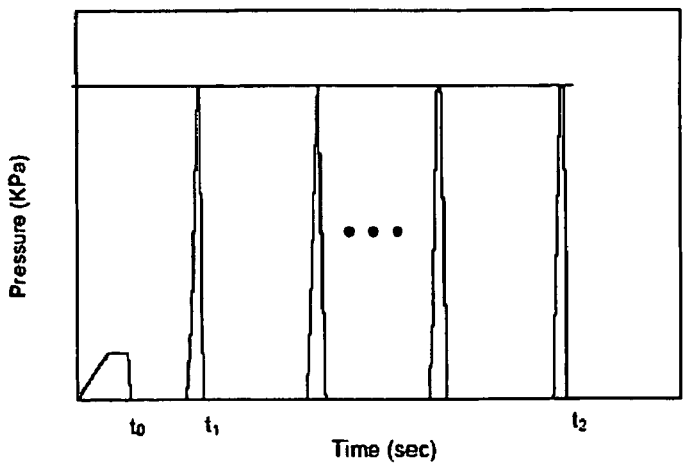
Figure 2A:
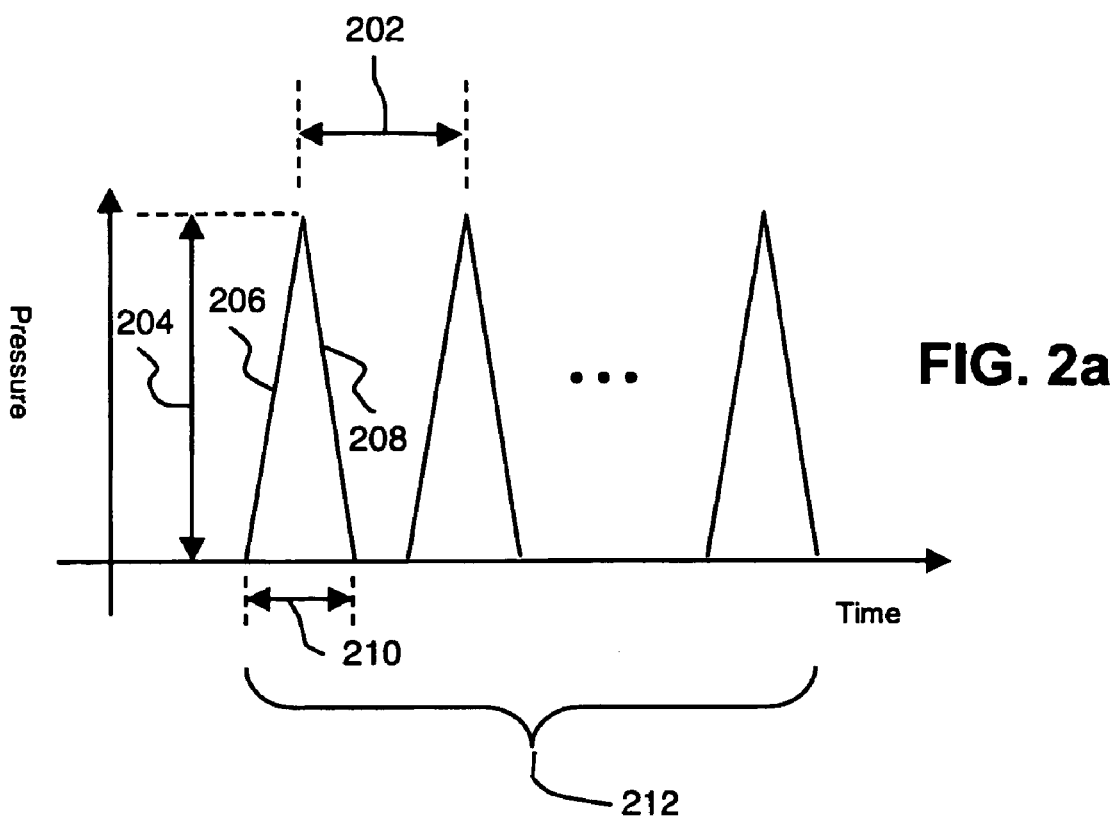
FIGS. 2$a$-2$d$ show the various profiles of pressure pulses and combinations thereof which maybe used for the separation process, in accordance with certain embodiments of the present invention.
Figure 2B:
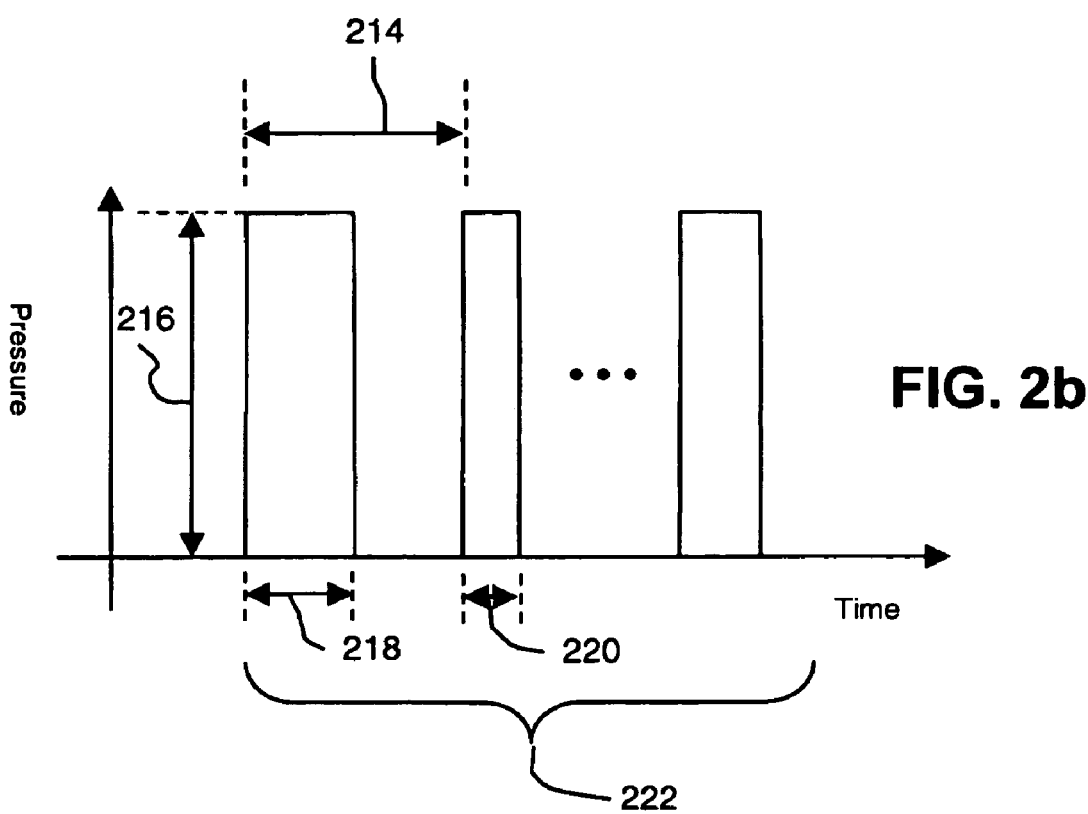
Figure 2C:
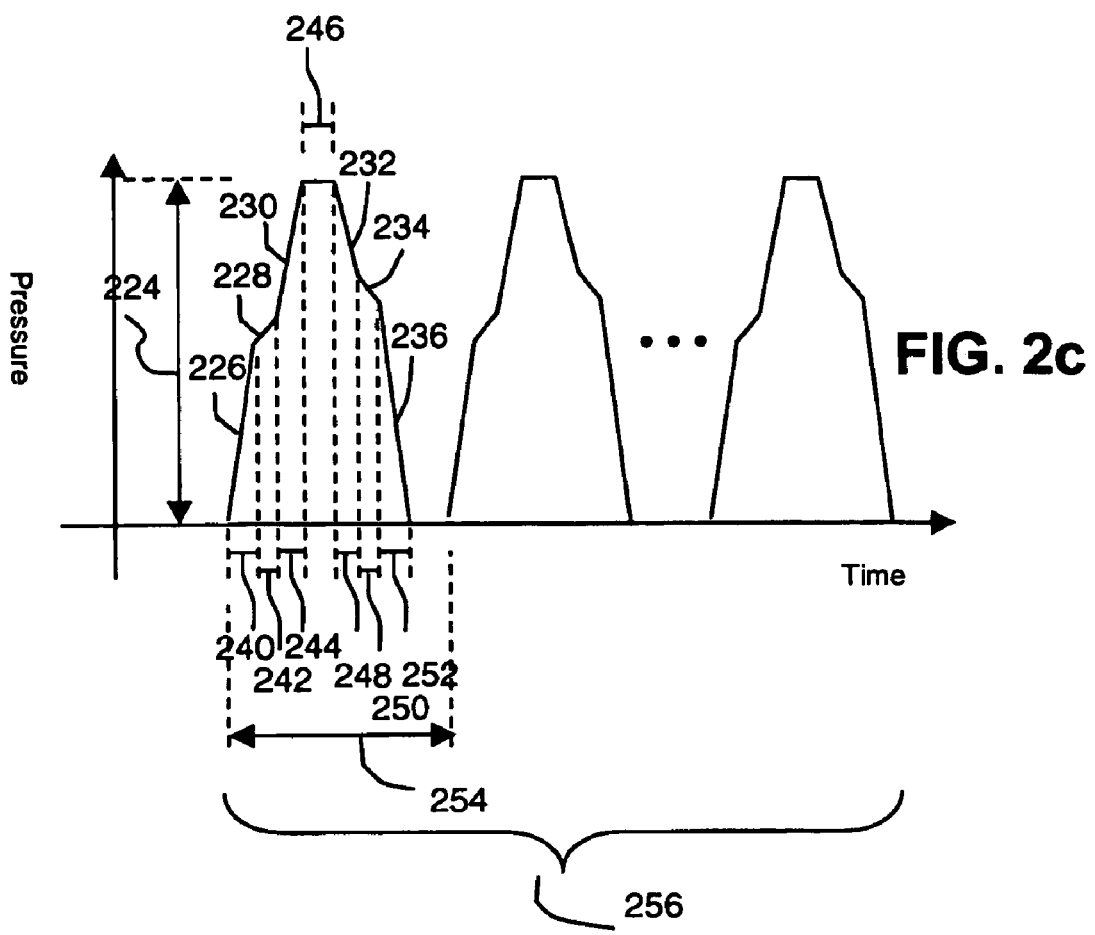
Figure 2D:
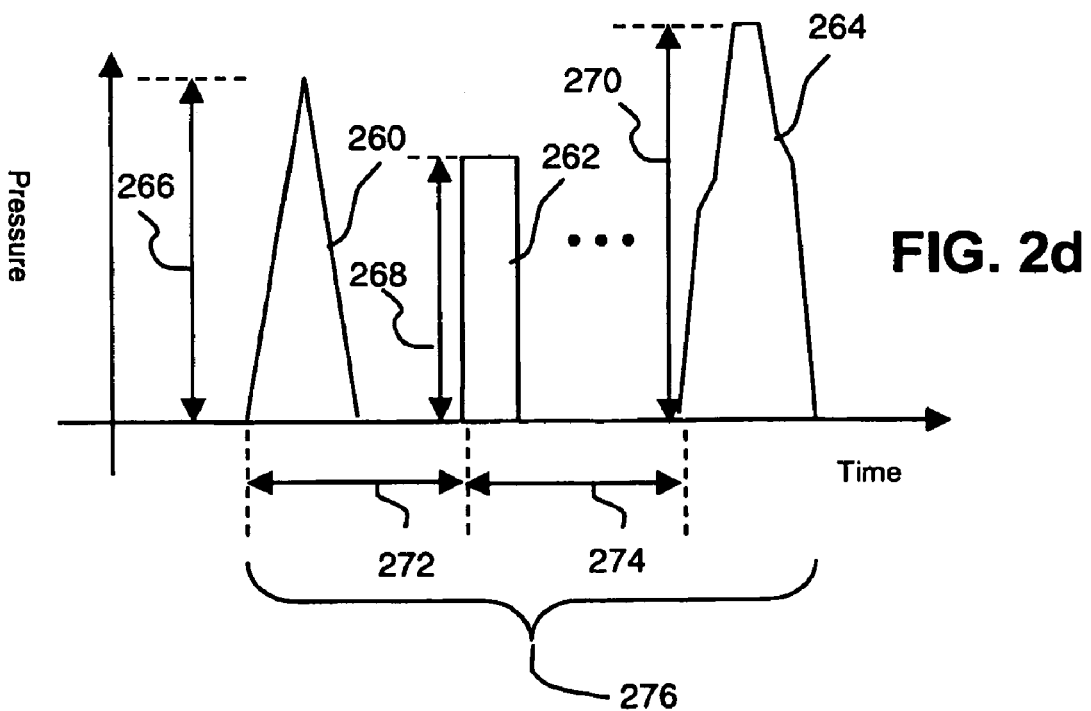

Broadly stated, certain embodiments of die present invention provide an on-chip bioparticle separator for an aqueous suspension, by applying a series of pressure pulses. Embodiments of the present invention use a series of pressure pulses for separating bioparticles on demand.

A key concept disclosed herein is the use of a precisely defined series of pressure pulses to separate bioparticles from biofluid on a biocompatible plastic substrate. When these short-duration, pressure pulses are applied to a plug of biofluid, the viscous drag, inertial force, and shear force on a particle inhibit it from achieving the same velocity as the surrounding liquid. Hence, after a series of pressure pulses, the suspended bioparticles are separated in the rear or the head of the liquid column.

Definitions

The term "pressure pulse" as used herein describes a single or plurality of precisely defined changes in pressure over a period of time delivered by the pressure source. The pressure pulse can be controlled by any electronic, chemical, thermal, pneumatic pressure generator coupled to a power supply or by designing a specific pressure source to deliver the desired characteristics. Furthermore, a wide variety profile of pressure pulses, such as the square wave pulse, half-square wave pulse, sine wave pulse, half-sine wave pulse, triangular pulse, half-triangular pulse, and multi-stage pulse, can be created by commonly available controllers.

The process of "Microfabrication" as described herein relates to the process used for manufacture of micrometer sized features on a variety of substrates using standard microfabrication techniques as understood widely by those skilled in this art. The process of microfabrication typically involves a combination of processes such as photolithography, wet etching, dry etching, electroplating, laser ablation, chemical deposition, plasma deposition, surface modification, injection molding, hot embossing, thermoplastic fusion bonding, low temperature bonding using adhesives and other processes commonly used for manufacture of MEMS (microelectromechanical systems) or semiconductor devices. "Microfabricated" or "microfabricated devices" as referred to herein refers to the patterns or devices manufactured using the microfabrication technology.

The term "chip", "microchip", or "microfluidic chip" as used herein means a microfluidic device generally containing a multitude of microchannels and chambers that may or may not be interconnected with each another. Typically, such biochips include a multitude of active or passive components such as microchannels, microvalves, micropumps, biosensors, ports, flow conduits, filters, fluidic interconnections, electrical interconnects, microelectrodes, and related control systems. More specifically the term "biochip" is used to define a chip that is used for detection of biochemically relevant parameters from a liquid or gaseous sample. The microfluidic system of the biochip regulates the motion of the liquids or gases on the biochip and generally provides flow control with the aim of interaction with the analytical components, such as biosensors, for analysis of the required parameter.

The term "microchannel" as used herein refers to a groove or plurality of grooves created on a suitable substrate with at least one of the dimensions of the groove in the micrometer range. Microchannels can have widths, lengths, and/or depths ranging from 1 µm to 1000 µm. It should be noted that the terms "channel" and "microchannel" are used interchangeably in this description. Microchannels can be used as standalone units or in conjunction with other microchannels to form a network of channels with a plurality of flow paths and intersections.

The term "microfluidic" generally refers to the use of microchannels for transport of liquids or gases. The microfluidic system consists of a multitude of microchannels forming a network and associated flow control components such as pumps, valves and filters. Microfluidic systems are ideally suited for controlling minute volumes of liquids or gases. Typically, microfluidic systems can be designed to handle fluid volumes ranging from the picoliter to the milliliter range.

The term "substrate" as used herein refers to the structural component used for fabrication of the micrometer sized features using microfabrication techniques. A wide variety of substrate materials are commonly used for microfabrication including, but not limited to silicon, glass, polymers, plastics, and ceramics to name a few. The substrate material may be transparent or opaque, dimensionally rigid, semi-rigid or flexible, as per the application they are used for. Generally, microfluidic devices consist of at least two substrate layers where one of the faces of one substrate layer contains the microchannels and one face of the second substrate layer is used to seal the microchannels. The terms "substrate" and "layer" are used interchangeably in this description. Specifically herein, the substrate is a material that can withstand the thermal dissociation temperature of the solid-propellant materials.

The intent of defining the terms stated above is to clarify their use in this description and does not explicitly or implicitly limit the application of the present invention by modifications or variations in perception of the definitions.

On-Chip Bioparticle Separator Using a Series of Pressure Pulses

Certain embodiments of the present invention provide an on-chip bioparticle separation scheme for microfluidic devices, which needs to be inherently suited to µTAS (Micro Total Analysis System). Also the series of pressure pulses generated to separate the bioparticle from biofluid should be precisely controlled. This approach gives the user fast and efficient results, avoids the use of specialized and bulky equipment, and is suited for integration into microfluidic devices for mass-production. This method allows the user to fabricate a functional on-chip bioparticle separator in a number of forms such as films, sheets and paste mixture along with an inert polymer.

Without wishing to be bound by a particular theory, generally speaking the principle of operation of various embodiments of the present invention may be described as follows: very small particles or microspheres in a moving liquid suspension experience a force governed by Stokes Law. It is primarily based on the radius of the microsphere and the viscosity of the surrounding liquid. For very small Reynolds number, Re, at the microfluidic level, the drag force on a microsphere in suspension is expressed as $F_d=6\pi\mu Vd$, where $F_d$ is the drag force of the fluid on a sphere, $\mu$ is the viscosity of the fluid, V is the velocity of the sphere relative to the liquid, and d is the radius of the sphere. In microfluidic devices, typically, the Reynolds number is much less than 1. At a very low Reynolds number, say $Re=10^{-3}$, the drag on a microsphere depends greatly on its distance from the channel walls. Conversely, at a Reynolds number of $10^4$, the drag is independent of that distance.

During flow of the biofluid, the drag on an individual bioparticle will be a function of its distance from the channel sidewalls. The closer the channel sidewall to a bioparticle, the higher the drag force on that bioparticle. The drag effect due to channel sidewall is specific only to microfluidic devices. In other words, the same drag effect would not be present in a macroscale device with much larger fluidic channels. Thus in microfluidic systems, suspended particles experience a high drag due to the small channel dimensions. The Diffusion coefficient of bioparticles plays an important role here. As described in J. Brody et al, *SPIE*, v 2978, 1997, the diffusion coefficients are inversely proportional to the size of the particles. Larger particles will have a smaller diffusion coefficient and smaller particles will have relatively larger diffusion coefficients. In addition, the shear rate on a particle in a suspension solution is proportional to the flow velocity of the solution. This implies that as velocity increases, particles will experience more shear drag and flow slower in relation to the rest of the surrounding liquid.

Figure 3A:
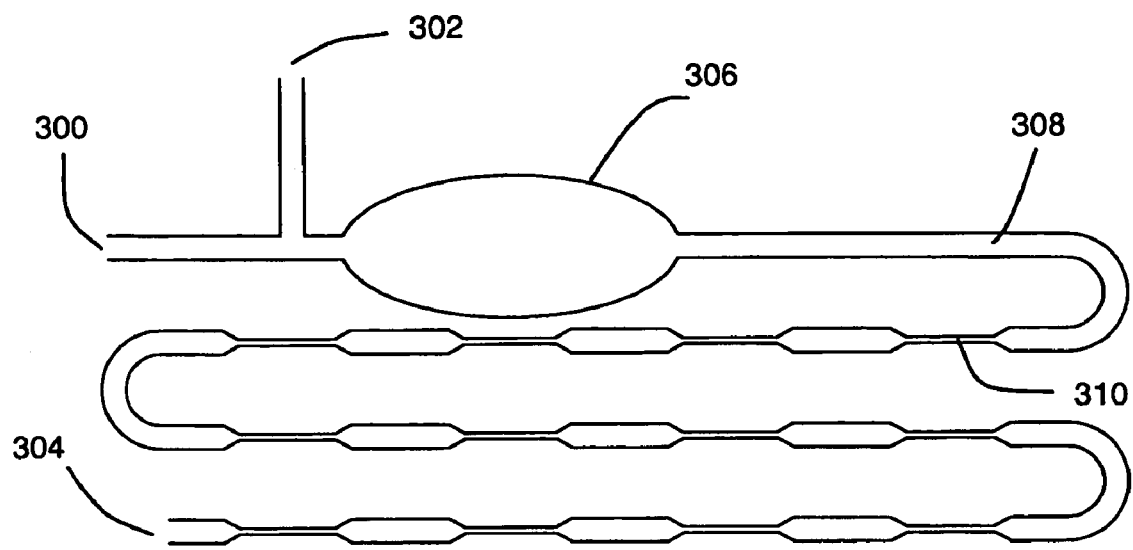
FIGS. 3$a$-3$d$ show various architectures of the microfluidic channel structures that may be used, in accordance with certain embodiments of the present invention.
Figure 3B:
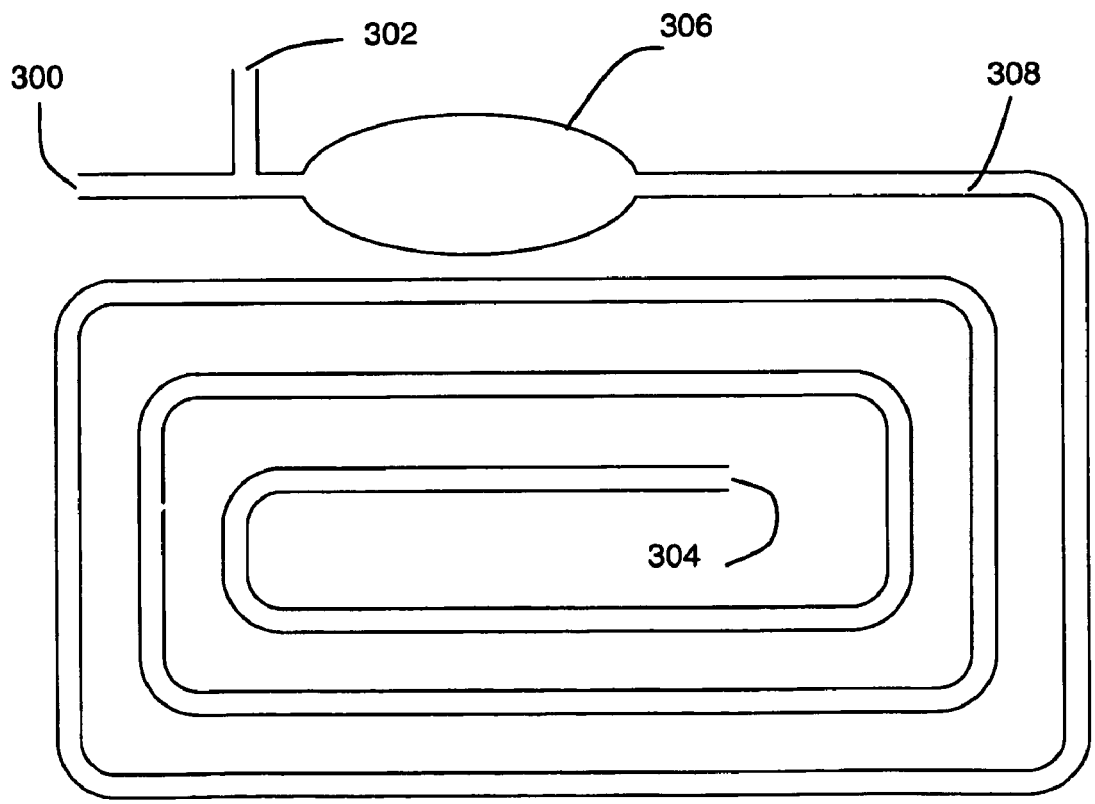
Figure 3C:
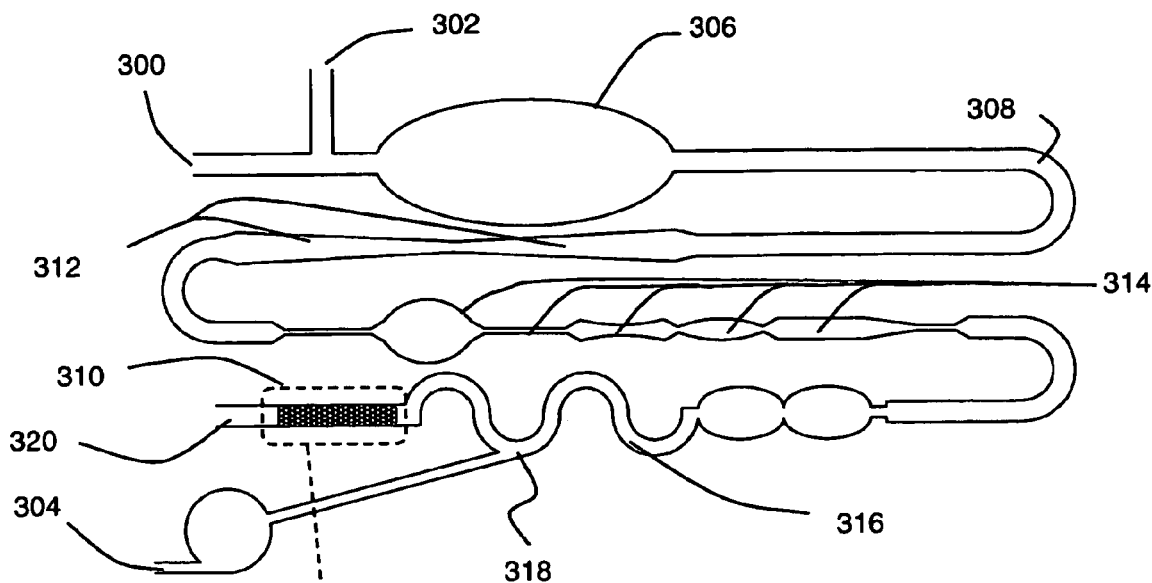
Figure 3D:
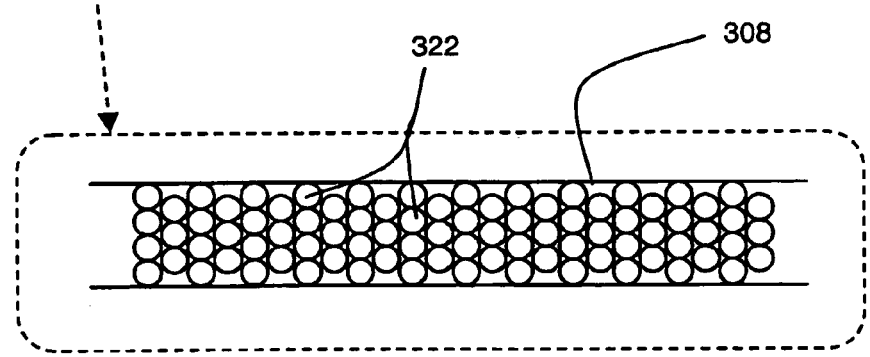

When a biofluid with bioparticles flows through a microchannel, the bioparticle will tend to move slower than the surrounding liquid. When a series of short-duration, high pressure pulses are applied to the plug, the viscous drag, inertial force and shear force on a particle inhibit it from achieving the same velocity as the surrounding liquid. Hence, after a series of pressure pulses, the suspended bioparticles accumulate towards the rear of the liquid column. So the speed and efficiency of separation is greatly improved with a series of pressure pulses, as compared with the separation; achieved by application of continuous pressure. The primary features of this separation; system are a long microchannel preceded by a microdispenser to reliably dispense a known volume into the microchannel upon which the pressure pulses can be applied.

A schematic sketch explaining the operation of an embodiment of the on-chip bioparticle separator using a series of pressure pulses is shown in FIG. 1*a* to FIG. 1*f*. FIG. 1*a* and FIG. 1*b* show the basic schematic of microdispenser structure where a biofluid with bioparticles 110 is introduced via a biofluid inlet 102, into a reservoir 106. A series of pressure pulses is applied through the pressure inlet 100 and pushes biofluid in the microchannel 108 toward the outlet port 104.

For operation, biofluid with bioparticles 110 is introduced into the biofluid inlet 102 at very low pressure. It enters the reservoir 106 and is prevented from exiting in the microchannel 108. The pressure inlet 100 has much smaller dimensions than the channel, and the biofluid is thus prevented from entering the pressure inlet 100 due to an available path of lesser resistance leading to the reservoir 106. FIG. 1*c* through FIG. 1*e* show a schematic sketch explaining the concept of bioparticle separation. As shown in FIG. 1*b*, the reservoir 106 is initially loaded with a biofluid with bioparticles. A precisely graduated volume of this biofluid is then ejected from the reservoir 106 at low velocity to ensure that no fluidic residue is left behind in reservoir 106 as shown in FIG. 1*c*. Next, a series of high pressure, short duration pulses 146 are applied to this liquid plug. As shown in FIG. 1*c*, FIG. 1*d*, and FIG. 1*e*, a series of pressure pulses causes the plug 120 to move and the bioparticles to accumulate towards the rear end of the liquid plug 140. FIG. 1*f* also shows a detailed view of the separation of bioparticles. FIG. 1*g* shows a schematic sketch of the series of applied pressure pulses. Note that the initial low pressure pulse (prior to $t_0$, is used for dispensing the biofluid out of the reservoir 106, and thereafter a series of high magnitude, short duration pulses are applied from $t_1$ to $t_2$ wherein these times correspond to the schematic sequences of FIG. 1*d* and FIG. 1*e*.

FIGS. 2*a*-2*d* show various profiles that can be used for the series of pressure pulses for an on-chip bioparticle separator. As shown in FIG. 2*a*, in accordance with an embodiment of the present invention, the shape of the series of pressure pulses is an approximately triangular pulse, which consists of magnitude 204, a rising section 206, a falling section 208, the on-time of the pulse 210, the peak-to-peak duration between the pulses 202, and the number of the pressure pulses 212. In accordance with an embodiment of the present invention, pressure pulses with magnitude 204 of approximately 5 KPa to 50 KPa (kilo Pascal) and peak-to-peak duration 202 of approximately 20 msec to 200 msec (milliseconds) are used. Residual pressure between each pulse is bled off in this duration. For a sequence of 10 to 50 pulses, the desired separation can be achieved in 5 to 150 sec.

In accordance with another embodiment of the present invention, the shape of the series of pressure pulses is rectangular, which consists of the pressure magnitude 216, the duration of the pulses 214, the number of the pressure pulses 222, and the same and/or different on-time of pulse 218, 220, as shown in FIG. 2*b*. In yet another embodiment, a more generic type of pressure pulses can be applied for the on-chip bioparticle separator, which is called the multi-stage pressure pulse. It has the pressure magnitude 224, various rising slopes 226, 228, 230 and various falling slopes 232, 234, 236 with respect to their duration 240, 242, 244, 246, 248, 250, and 252 respectively, the duration between the pulses 254, and the number of the pulses 256, as shown in FIG. 2*c*. In yet another embodiment a combination of the different type of pressure pulses, for instance, triangular 260 and/or rectangular 262 and/or generic type pulses 264 with various magnitudes 266, 268, 270 may be applied. The applied pressure pulse may also have the same and/or different duration between pulses 272, 274, for the total number of pulses 276.

The various cross-sections of the microchannel that can be used include, but are not limited to, rectangular or circular or trapezoidal, and so on. For a hydrophobic substrate with a rectangular cross-section of the microchannel, when a liquid encounters an abrupt change in channel width, from large to small, a positive pressure is required to push the liquid across the restriction. As described in *C. Ahn* et al, μTAS, 2000, this pressure can be given: $\Delta P=2\sigma\cos(\Theta c)\,[(1/w1+1/h1)-(1/w2+1/h2)]$, wherein; w1, h1 and w2, h2 are the width, height of the wide microchannel and the narrow microchannel respectively, Θc is the contact angle, σ is the surface tension of the liquid/air interface and ΔP is the pressure required to push the liquid into the narrow channel. The geometry of the reservoir decides the volume of dispensed liquid. In accordance with an embodiment of the present invention, the volume of the reservoir ranges from 10 nanoliter to 10 microliter as determined by the volume of the reservoir. The passive valve at the outlet of the reservoir is 40 μm wide and the following microchannel is approximately 50 μm in depth and 1 mm in width. The total length of the microchannel is from 10 cm to 100 cm.

Some of the microfluidic components that can be used especially include, but are not limited to, a wide variety of valves such as passive and/or active valves and dispensers. FIG. 3*a* shows a series of passive valves 310 incorporated into the microchannels, which provide for a rapid rise in flow velocity when the liquid, upon exiting from the passive valve, enters into the wider microchannel. This would be expected to provide a flow 'spike'. In accordance with an embodiment of the present invention, the distance between two successive passive valves is $1/10^{th}$ to $1/2^{th}$ of plug length, wherein the plug length is defined as the length occupied by the liquid column as it is ejected from the dispensing reservoir 306 and fills the subsequent microchannel 308. It is expected that each valve would provide a spike in the flow rate of the liquid flowing through it. With a series of such spikes in flow rates, it is envisaged that separation could possibly be achieved with a single large pressure pulse or with constant pressure flow. The passive valves can range in width from approximately 10 to 490 micrometers, when the microchannel is approximately 500 micrometers wide.

In another embodiment of the present invention, the various shapes of the microchannel 308 that may be used include, but are not limited to, a rectangular-spiral shape, as shown in FIG. 3*b*, or a circular- or an oval-spiral shape or a triangular-spiral shape, and so on. In another embodiment of the present invention, the combination of various shapes of the microchannel with each section of different width can be used, such as a part of the microchannel with increasing and/or decreasing channel widths 312, 314, a sine-wave-like channel 316, and so on, as shown in FIG. 3*c*, including a reservoir 304 which can be used to gather bioparticles after separation, and especially a packed bed column 310 by a dense porous nano/micro-structure 322 through the microchannel 308, of which the morphology is very useful as preconcentrators and microreactors as well as chromatographic separation columns in chemical and biological application, as shown in FIG. 3d.

Figure 4A:
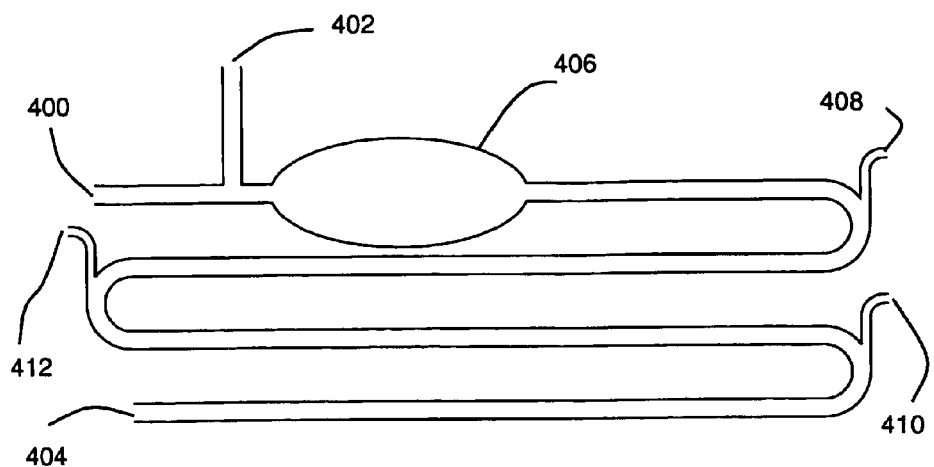
FIGS. 4$a$-4$b$ show schematic sketches illustrating the use of multiple inlets for applying the aforementioned pressure pulses and their locations with respect to the microfluidic channel network, in accordance with certain embodiments of the present invention.
Figure 4B:
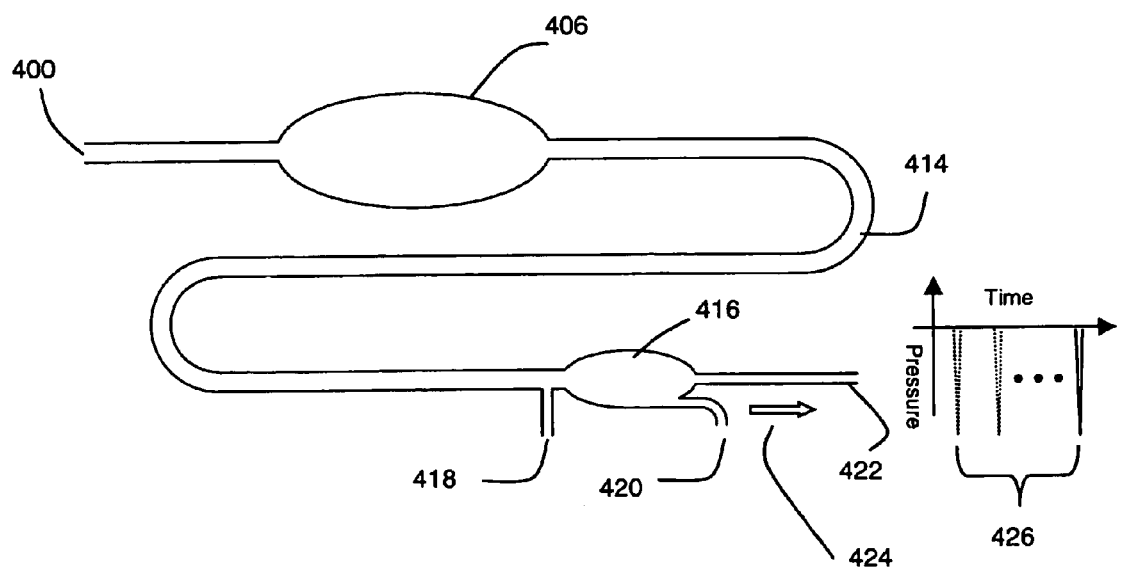

In yet another embodiment of the present invention, a plurality of locations for applying a series of pressure pulses may be used. FIG. 4a shows one of the examples of various locations for pressure inlets 400, 408, 410, 412. Furthermore, in yet another embodiment of the present invention, a series of negative pressure pulses 426, as shown in FIG. 4b, may be used for the scheme of a filter-less bioparticle separator. A biofluid sample in the reservoir 406 which is injected through the biofluid inlet 400 can be "pulled out" by a series of negative pressure pulses 426 applied at the pressure inlet 422. Furthermore, as shown in FIG. 4b, an additional reservoir 416 may be used to collect the "front end" of the suspension, which is purged of microparticles, and by using positive pressure at yet another pressure inlet 416, this solution may be transferred to a separate outlet 420.

Some of the substrate materials that may be used include, but are not limited to, Silicon or a derived Silicon surface such as Silicon dioxide or Silicon Nitride, glass, quartz, ceramics, a wide variety of polymers such as PDMS, PMMS, PC, COC, or a combination of listed substrates such as a glass substrate with a coated film of PMMA on the surface. In accordance with an embodiment of the present invention, a low-cost plastic surface is used for fabricating the on-chip bioparticle separator using a series of pressure pulses for a disposable biochip. The substrate material may have a thickness ranging from 100 μm to 5 mm. The thickness of the substrate material should be sufficient to impart dimensional stability required for the various steps of the microfabrication process. Generally, the surface has a hydrophobic surface characteristic specifically for the passive microfluidic dispensing schemes. The concepts of the passive microvalves and the on-chip dispensers are clearly detailed in U.S. Provisional Patent Application 60/204,214 filed on May 12, 2000, U.S. Provisional Patent Application 60/209,051 filed on Jun. 2, 2000, and U.S. patent application Ser. No. 10/602,575 filed on Jun. 24, 2003, all of which are incorporated herein by reference in their entirety. The surfaces of the above listed substrates may be easily modified by a variety of surface modifications techniques such as plasma treatment, plasma deposition, covalent cross-linking etc. that are well known in the art. Depending on the application, the biocompatibility characteristics of the substrate may be an important factor in determining choice of substrate material. Broadly stating, any substrate material that can be handled using established microfabrication processes may be used.

Figure 5A:
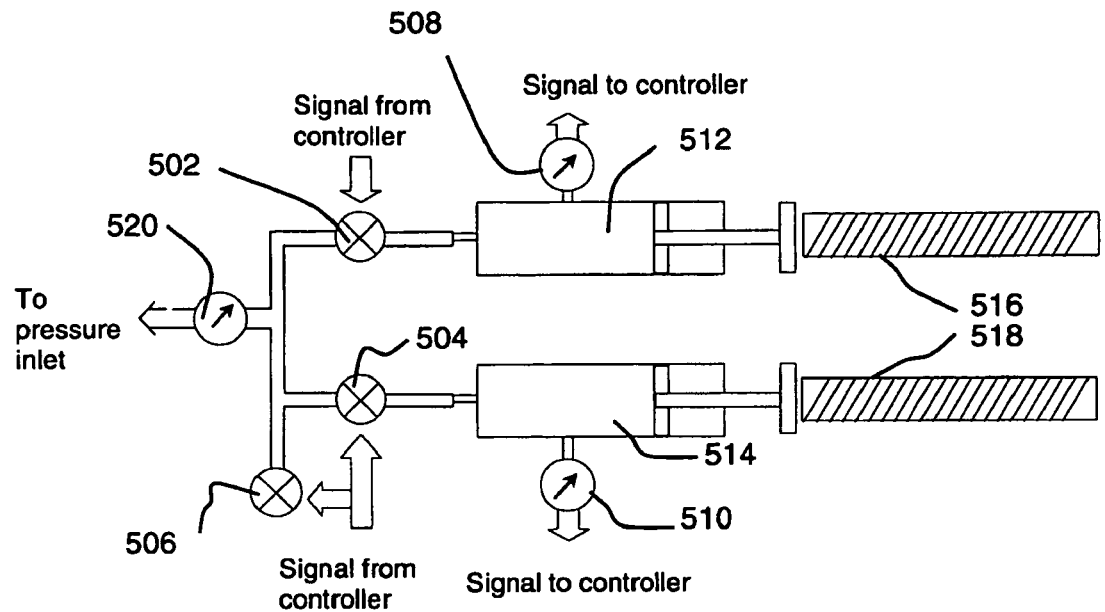
FIGS. 5$a$-5$c$ show a schematic of the apparatus for the on-chip bioparticle separator wherein the pressure delivery system is not integrated with the biochip, in accordance with certain embodiments of the present invention.
Figure 5B:
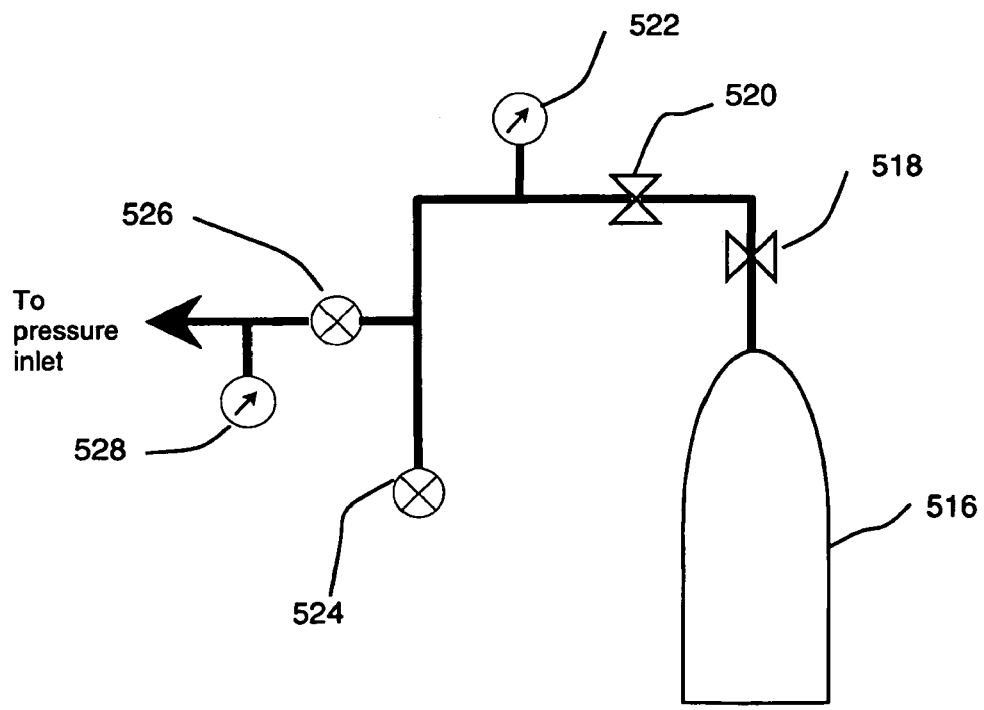
Figure 5C:
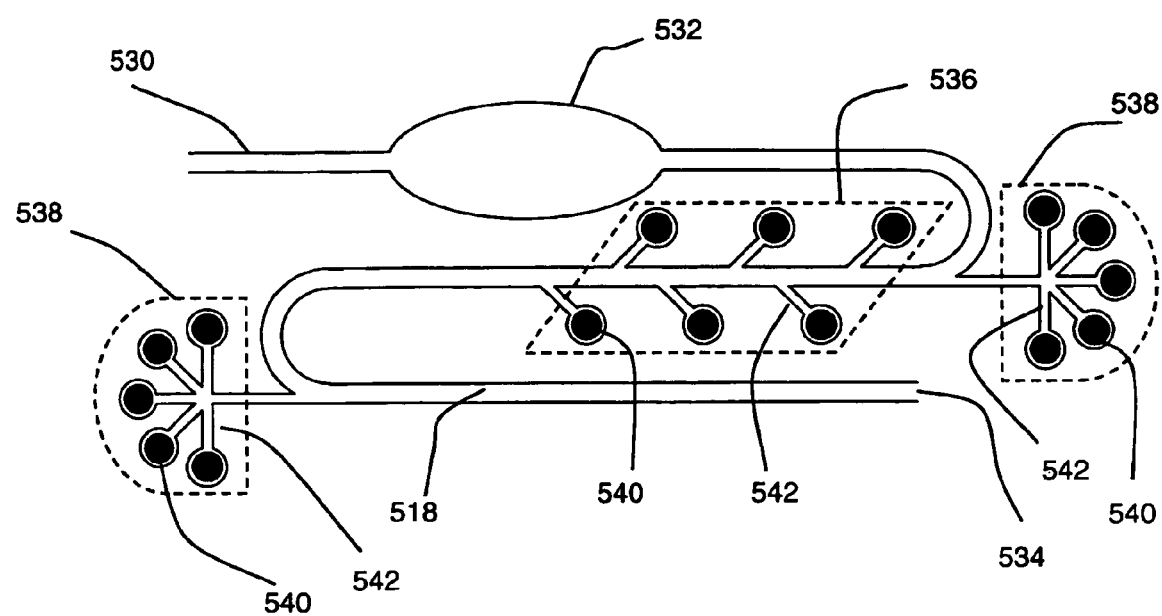

The apparatus for generating a series of pressure pulses is designed with the facility to apply a desired pressure for a desired time duration to the pressure inlet of the biochip. FIGS. 5a-5c show the schematic of the apparatus, in accordance with certain embodiments of the present invention. As shown in FIG. 5a the precision driving screws 516, 518 are gradually rotated to build pressure in the syringes 512, 514. The chambers of the syringes are directly connected to the inlets of pressure sensors 508, 510 with a sensing range of 0 to 50 kPa. The outlets of the syringes lead to inlets of solenoid valves 502, 504. The valves 502, 504 are either on (open) or off (closed). With no power, the valves are normally off, that is, closed. The outlets of the valves lead to a chamber (common point) at which another pressure sensor 520 is connected. This sensor 520 is meant to provide a reading of the actual pressure applied to the pressure inlet of the on-chip bioparticle separator. In another embodiment, as shown in FIG. 5b, a high-pressurized tank 516 of approximately 450 to 3000 psi, one and/or more than one regulators) 518, 520 for decreasing pressure, electrically motivated flow control valves 524, 526 and precision pressure sensors 522, 528 for monitoring and/or feedback control may be used. In yet another embodiment, FIG. 5c shows precision pressure pulse arrays 536, 538 located at appropriate positions along the microchannel 518. In these arrays a suitable solid-propellant material 540 can be deposited and connected through microchannel branches 542. The use of solid propellants for on-chip microfluidic manipulation is disclosed in U.S. patent application Ser. No. 10/946,818, incorporated herein in its entirety by reference.

The control apparatus has a DAQ (Digital Acquisition) board to interface with the control software. In accordance with an embodiment of the present invention, PC based control software such as LabVIEW™ is used to provide a graphical user interface (GUI) to read data from pressure sensors and control operation of valves in real-time. The interface has provision to control the on/off condition of each solenoid valve. The on-time and duration for each valve may be specified. For example, if a valve needs to be turned on or opened at 5 seconds after start of program, the on-time is entered as 5000 ms. If the valve needs to be held open for 100 ms and then closed, off-time is entered as 5100 ms. This means the valve will open at 5000 ms from the start of program, and close at 5100 ms from the start of program, providing an open time of 100 ms. The readouts of pressure sensors are also displayed in real-time. The reading from the pressure sensors may be simultaneously stored in a text file for later analysis if needed. There is a provision for 'looping' the program, which is useful when the cycle needs to be run multiple times for delivering a series of pressure pulses. In another embodiment, some of the pressure systems that may be used include, but are not limited to pressurized tanks, or a micro sized pump such as solid and/or liquid propellant, or a precision detonator to generate pressure pulses, or a dedicated ASIC as an interface controller.

Figure 6A:
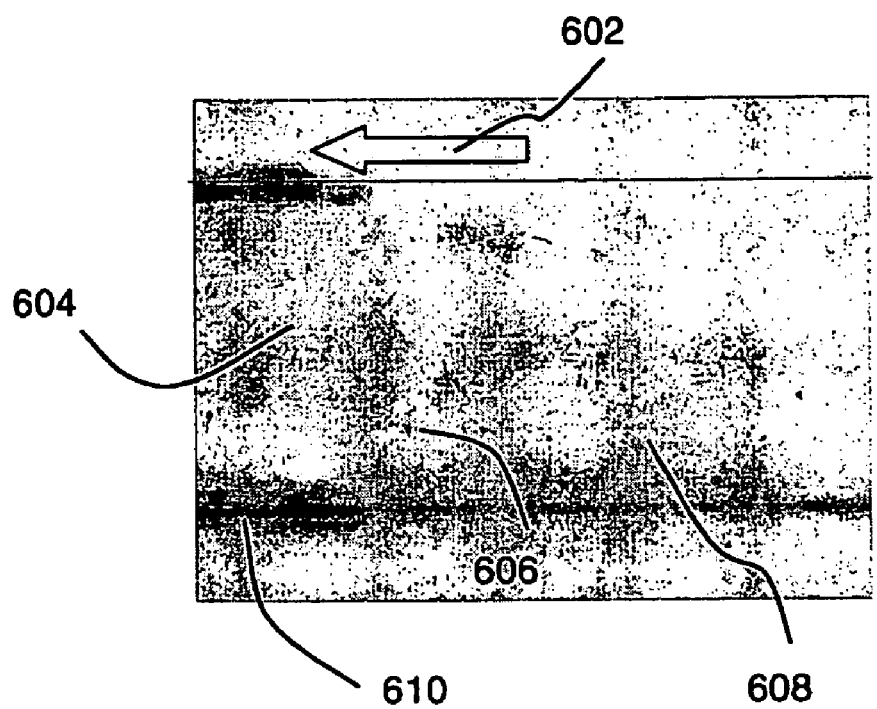
FIGS. 6$a$-6$b$ show micro-photographs of a typical result of the on-chip bioparticle separator using a series of pressure pulses, in accordance with an embodiment of the present invention.
Figure 6B:
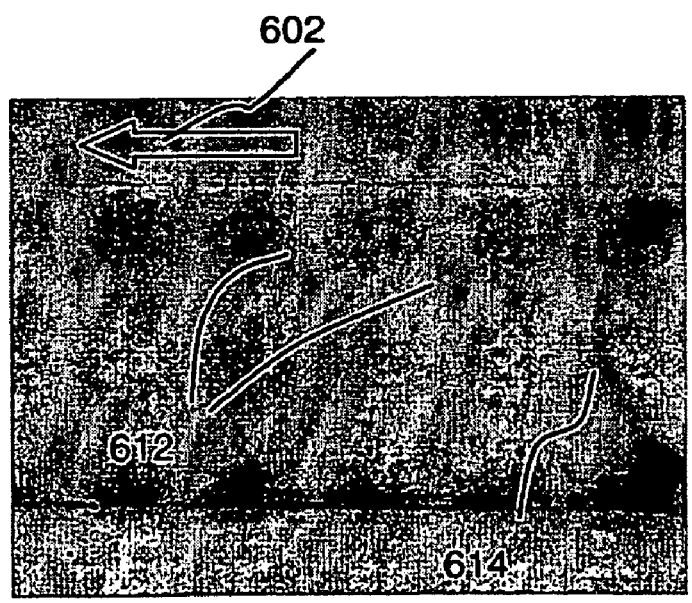

Microphotographs as test results of the front end and rear end of the suspension solution plug in the microchannel 610 are shown in FIGS. 6a-6b. As FIG. 6a clearly shows, the front end 604 of the solution plug 608 is purged of bioparticles while bioparticles 612 are accumulated at the rear end 614 in flow direction 602 as shown in FIG. 6b. The movement of the liquid plug through the microchannel and the separation of the bioparticles are visually monitored using a high resolution microscope, along with a scale to measure the length of liquid plug cleared of bioparticles. The total length of the dispensed biofluid plug and the length of liquid visibly clear of bioparticles are measured to calculate the volume of liquid purged of bioparticles. After applying a desired number of pulses, the device is taken under a high-resolution microscope and the length of liquid column visibly free of beads was measured as a percentage of the total length of dispensed solution.

Figure 7A:
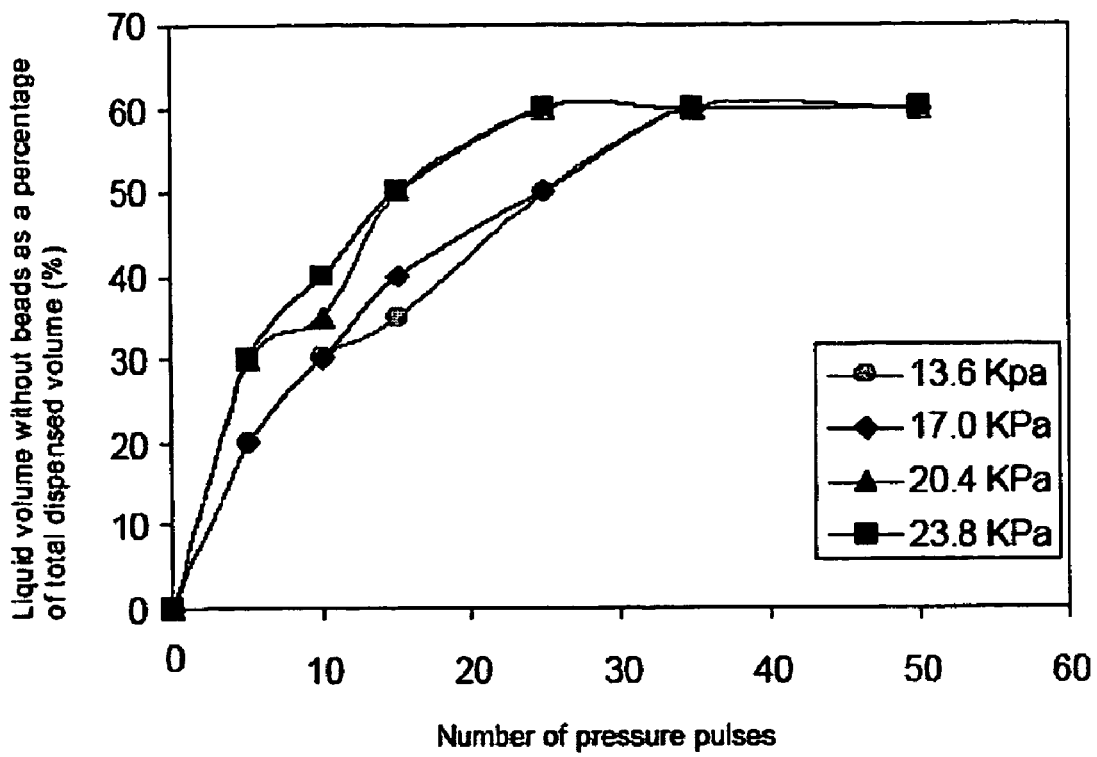
FIGS. 7$a$-7$b$ show characterization results of the on-chip bioparticle separator using a series of pressure pulses, such as percentage of solution purged of bioparticles as a function of the number of pressure pulses, and as a function of the applied pressure pulses, in accordance with certain embodiments of the present invention.
Figure 7B:
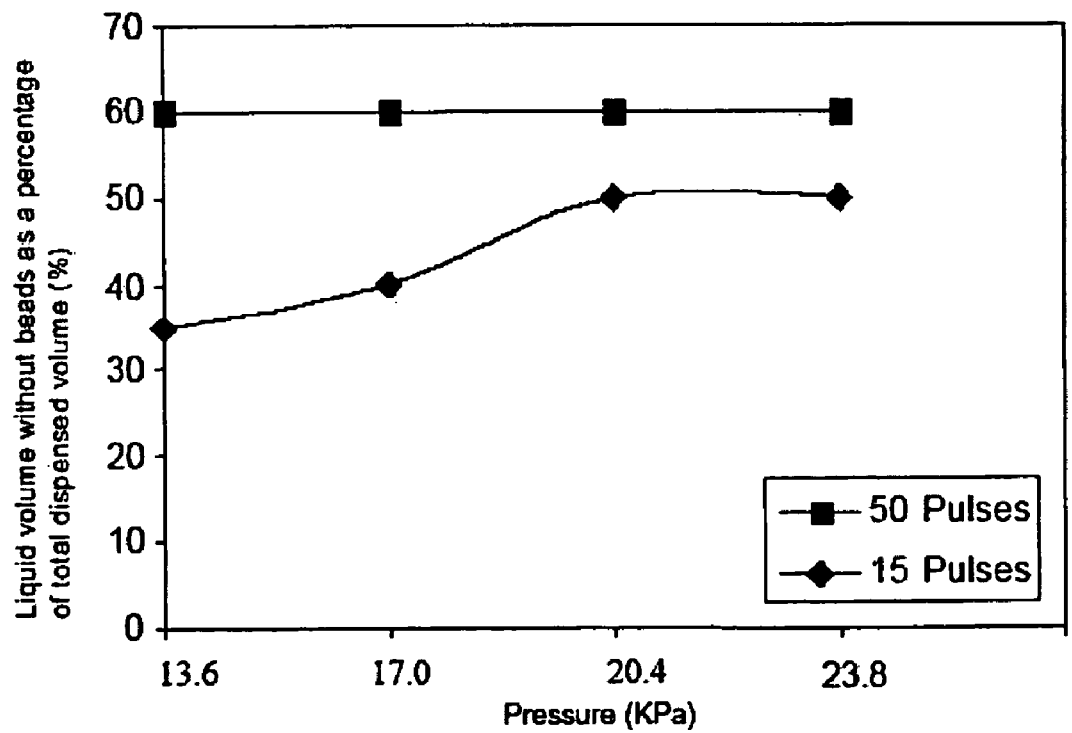

Characterization results are shown in FIGS. 7a-7b. FIG. 7a shows that, for a given pressure, increasing the number of pulses results in more separation. The final degree of separation is directly proportional to the number of pressure pulses. This is true only until maximum achievable separation, or separation saturation, is reached. Once that level of separation is reached, applying pressure pulses further does not increase the degree of separation any more. For higher input pressures, the maximum separation is achieved with a lower number of pulses. As shown in FIG. 7b, with a low number of applied pulses, the inlet pressure has a significant impact on the separation achieved. However, for a very large number of pulses, the percentage separation is essentially independent of pressure and maximum achievable separation is seen at low pressure. A desired dynamic pressure characteristic can be realized by optimizing the inlet pressure and number of pulses to achieve maximum separation in a relatively short time.

Certain embodiments of the aforementioned on-chip bioparticle separator using a series of pressure pulses offers numerous advantages for microfluidic manipulation, a few of which are enumerated hereafter.

Certain embodiments of the present invention provide the ability to fabricate a fully integrated separation mechanism for microfluidic chips.

Certain embodiments of the present invention provide the ability to fabricate an integrated separator without using complex fabrication techniques.

Certain embodiments of the present invention provide ease of integration with a disposable microfluidic system.

Certain embodiments of the present invention realize a reliable actuation scheme due to lack of bulky parts in the pressure source, wherein solid propellant based actuators are used as an on-chip pressure source.

Certain embodiments of the present invention provide the ability to generate rapid separations of bioparticles from suspensions for a microfluidic biochip.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method to separate particles suspended in a fluid, said method comprising:
    loading a micro-dispenser with a predetermined volume of said fluid containing said suspended particles;
    ejecting said predetermined volume of said fluid containing said suspended particles from said micro-dispenser into a micro-channel of substantially constant diameter to form a liquid plug within said micro-channel, said liquid plug having a first end and a second end; and
    applying at least one pressure pulse to said liquid plug within said micro-channel to cause said liquid plug to move along said micro-channel and said suspended particles to accumulate toward said first end of said liquid plug.

2. The method of claim 1 wherein said loading comprises applying said fluid containing said suspended particles to an inlet port of said micro-dispenser.

3. The method of claim 1 wherein said ejecting comprises releasing a first volume of pressurized gas at a first pressure level into an inlet port of said micro-dispenser for a first predetermined period of time.

4. The method of claim 3 wherein said applying at least one pressure pulse comprises releasing a second volume of pressurized gas at a second pressure level into said inlet port of said micro-dispenser for a second predetermined period of time.

5. The method of claim 4 wherein said second pressure level is greater than said first pressure level.

6. The method of claim 4 wherein said second predetermined period of time is less than said first predetermined period of time.

7. The method of claim 1 further comprising tapping off, from an outlet port of said micro-channel, a portion of said liquid plug that is toward said second end of said liquid plug and that is free of said suspended particles.

8. The method of claim 7 further comprising analyzing said portion of said liquid plug to determine at least one characteristic of said portion of said liquid plug.

9. The method of claim 1 wherein said fluid comprises whole blood.

10. The method of claim 1 wherein said suspended particles comprise blood cells.

11. The method of claim 7 wherein said, portion of said liquid plug comprises blood plasma.

* * * * *